(12) United States Patent
Jiaang et al.

(10) Patent No.: US 7,425,633 B2
(45) Date of Patent: Sep. 16, 2008

(54) PYRROLIDINE COMPOUNDS

(75) Inventors: Weir-Torn Jiaang, Taichung (TW); Yu-Sheng Chao, Warren, NJ (US); Hsing-Pang Hsieh, Taipei (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 11/510,973

(22) Filed: Aug. 28, 2006

(65) Prior Publication Data

US 2007/0082932 A1  Apr. 12, 2007

Related U.S. Application Data

(60) Provisional application No. 60/711,751, filed on Aug. 26, 2005.

(51) Int. Cl.
*C07D 401/12* (2006.01)
*C07D 277/02* (2006.01)
*C07D 263/04* (2006.01)
*C07D 207/04* (2006.01)
*C07D 403/12* (2006.01)

(52) U.S. Cl. .................. 546/208; 546/209; 546/210; 548/200; 548/215; 548/314.7; 548/518

(58) Field of Classification Search .................. 548/518
See application file for complete search history.

(56) References Cited

FOREIGN PATENT DOCUMENTS

WO  WO 2004/016587 A1  2/2004
WO  WO 2005/007316 A1  8/2005

OTHER PUBLICATIONS

Type 2 diabetes [online], [retrieved on Oct. 26, 2007]. Retrieved from the Internet, URL; http://www.mayoclinic.com/health/type-2-diabetes/DS00585>.*
Diabetes mellitus type 2 [online], [retrieved on Oct. 26, 2007]. Retrieved from the Internet, URL; http://en.wikipedia.org/wiki/Diabetes_mellitus_type_2>.*
CAPLUS, retrieved on May 13, 2008, Accession No. 2005:729632, Document No. 143:194237.*

* cited by examiner

*Primary Examiner*—Kamal Saeed
*Assistant Examiner*—Shawquia Young
(74) *Attorney, Agent, or Firm*—Occhiuti Rohlicek & Tsao LLP

(57) ABSTRACT

A compound of the following formula:

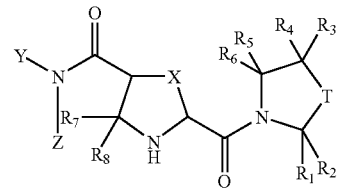

wherein $R_1$, $R_2$, $R_3$, $R_4$, $R_5$, $R_6$, $R_7$, $R_8$, T, X, Y, and Z are as defined herein. Also disclosed is a method for inhibiting dipeptidyl peptidase IV or for treating Type II diabetes with such a compound.

25 Claims, No Drawings

SEQUENCE LISTING

```
<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: Primer

<400> SEQUENCE: 1
aagcttccat ggcagcagca atggaaaca                                    29

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
gcggccgctt atatcacttt tagagcagca ata                               33
```

PYRROLIDINE COMPOUNDS

RELATED APPLICATION

This application claims priority to U.S. Provisional Application No. 60/711,751, filed on Aug. 26, 2005, the contents of which are incorporated herein by reference.

BACKGROUND

Glucagon-like peptide-1 (GLP-1) is a gut hormone produced by intestinal endocrine L-cells in response to nutrient ingestion. GLP-1 inhibits glucagon secretion and stimulates glucose-dependent insulin release from the pancreas. It was observed that administration of GLP-1 significantly lowered blood glucose levels in Type II diabetes patients (Zander M, et al. *Lancet* 2002, 359: 824-830).

However, GLP-1, whether endogenously or exogenously administered, degrades rapidly. (Kieffer T. J., et al. *Endocrinology* 1995, 136: 3585-3596; and Mentlein R, et al. *Eur. J. Biochem.* 1993, 214: 829-839). The degradation is attributable to dipeptidyl peptidase IV (DPP-IV), a member of the prolyl peptidase family. Recent clinical data indicate that inhibiting DPP-IV results in enhanced insulin secretion, reduced plasma glucose concentrations, and improved pancreatic β-cell function (Pederson R. A., et al. *Diabetes* 1998, 47: 1253-1258; and Ahren B, et al. *Diabetes Care* 2002, 25: 869-875). Thus, inhibitors of DPP-IV are potential drug candidates for Type II diabetes.

SUMMARY

This invention is based on an unexpected finding that a group of diamide compounds effectively inhibit the activity of DPP-IV. One aspect of this invention relates to a diamide compound of the following formula:

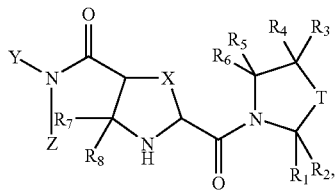

wherein T is $C(R_9R_{10})$, NH, O, or S; X is $(CR_{11}R_{12})_n$, n being 1 or 2; each of Y and Z, independently, is H, alkyl, cycloalkyl, heterocycloalkyl, aryl, heteroaryl, arylalkyl, carbonyl, or hydroxyl, or Y and Z together with the N atom to which they are attached form a 5 or 6 membered ring, which is optionally substituted with alkyl, aryl, halo, hydroxyl, akyloxyl, nitro, amino, alkoxycarbonyl, or carboxy, optionally fused with a 3-8 membered aromatic or non-aromatic ring containing 0, 1, 2, or 3 heteroatoms; and each of $R_1$, $R_2$, $R_5$, $R_6$, $R_7$, and $R_8$, independently, is H, alkyl, cyano, nitro, alky, cycloalkyl, heterocycloalkyl, aryl or heteroaryl; each of $R_3$, $R_4$, $R_9$, $R_{10}$, $R_{11}$, and $R_{12}$, independently, is H, alkyl, halo, cyano, nitro, alkoxyl, hydroxyl, cycloalkyl, heterocycloalkyl, aryl or heteroaryl.

Referring to the diamide compounds of the above formula, a subset features that X is $CH_2$, $CH_2CH_2$, or $C(CH_3)_2$. In these compounds, Y can be phenyl, alkaryl, or cycloalkyl; or Y and Z together with the nitrogen atom to which they are attached can be isoindolinyl or 1,2,3,4-tetrahydroisoquinolinyl, optionally substituted with alkyl, aryl, halo, hydroxyl, akyloxyl, nitro, amino, akoxycarbonyl, or carboxy; T can be O, S, or $CH_2$; $R_1$ can be cyano, and each of $R_2$, $R_3$, $R_4$, $R_5$, $R_6$, $R_7$, $R_8$, $R_9$, $R_{10}$, $R_{11}$ and $R_{12}$ can be H; $R_3$ can be F, $R_4$ can be H or F, and $R_2$, $R_3$, $R_4$, $R_5$, $R_6$, $R_7$, $R_8$, $R_9$, $R_{10}$, and $R_{11}$ can be H; or $R_7$ is $CH_3$ and $R_8$ is H or $CH_3$.

Shown below are exemplary compounds of this invention:

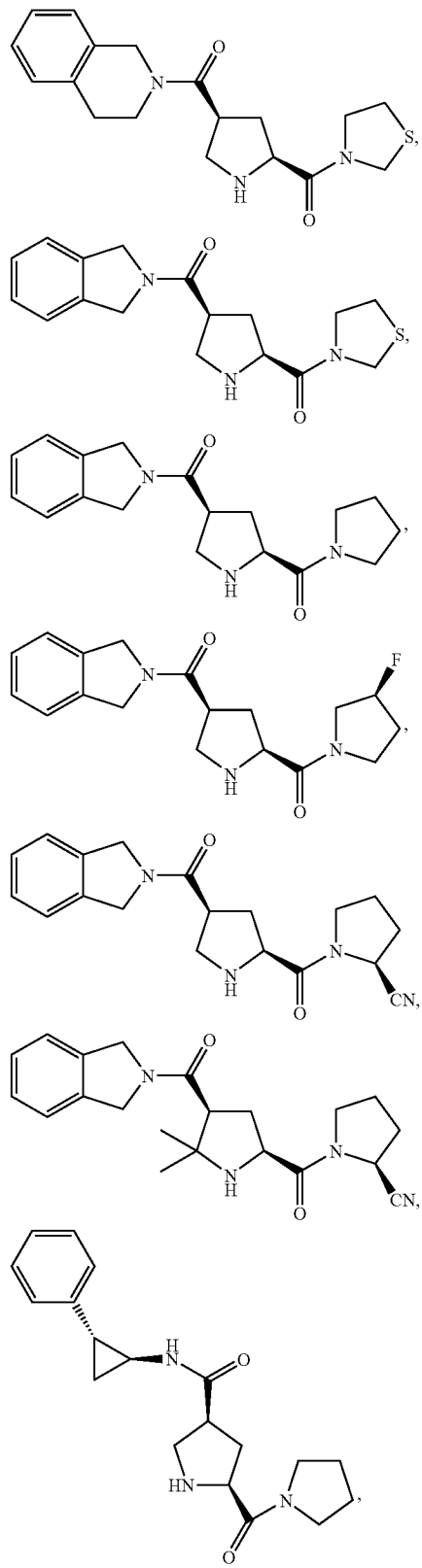

-continued

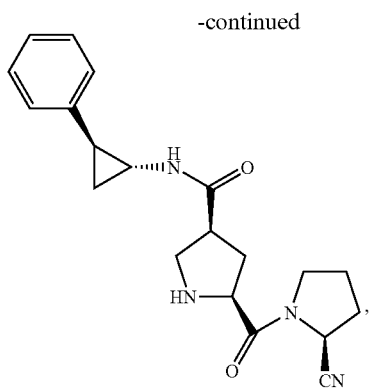

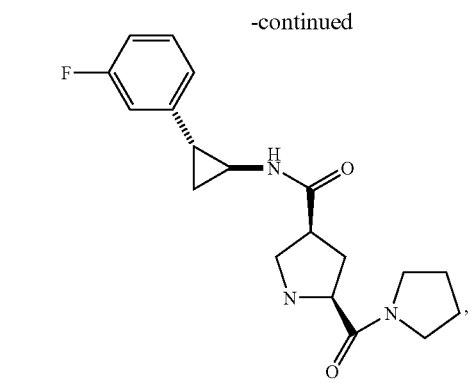

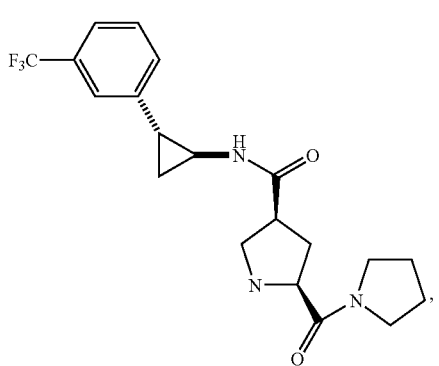

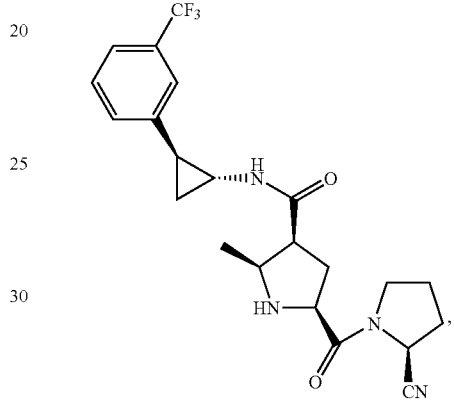

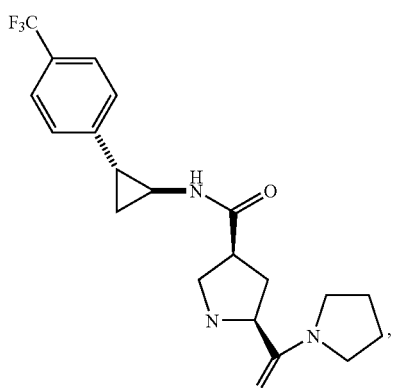

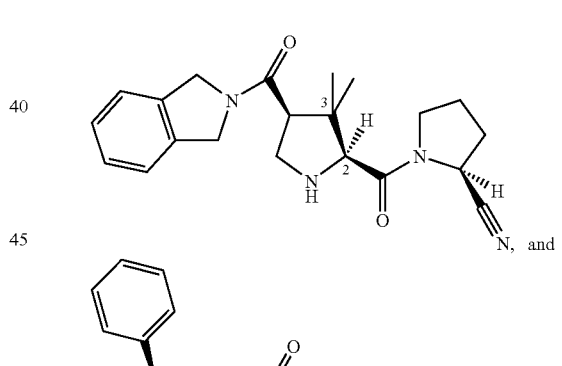

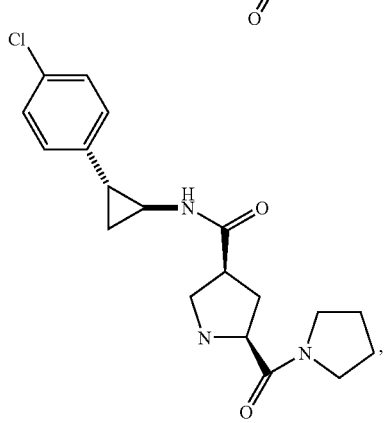

The term "heteroatom" herein refers to a non-carbon atom. Examples of hetereatoms, include, but are not limited to, N, O, and S.

The term "alkyl" herein refers to a straight or branched hydrocarbon, containing 1-10 carbon atoms. Examples of alkyl groups include, but are not limited to, methyl, ethyl, n-propyl, i-propyl, n-butyl, i-butyl, and t-butyl. The term "alkoxy" refers to an —O-alkyl. The term "alkoxyalkyl"

refers to an alkyl group substituted with one or more alkoxy groups. The term "haloalkyl" refers to an alkyl group substituted with one or more halo groups. The term "hydroxyalkyl" refers to an alkyl group substituted with one or more hydroxy groups.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl. The term "aryloxy" refers to an —O-aryl. The term "aralkyl" refers to an alkyl group substituted with an aryl group.

The term "cycloalkyl" refers to a saturated and partially unsaturated cyclic hydrocarbon group having 3 to 12 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having one or more heteroatoms (such as O, N, or S). Examples of heteroaryl groups include pyridyl, furyl, imidazolyl, benzimidazolyl, pyrimidinyl, thienyl, quinolinyl, indolyl, and thiazolyl. The term "heteroaralkyl" refers to an alkyl group substituted with a heteroaryl group.

The term "heterocycloalkyl" refers to a nonaromatic 5-8 membered monocyclic, 8-12 membered bicyclic, or 11-14 membered tricyclic ring system having one or more heteroatoms (such as O, N, or S). Examples of heterocycloalkyl groups include, but are not limited to, piperazinyl, pyrrolidinyl, dioxanyl, morpholinyl, and tetrahydrofuranyl.

Alkyl, cycloalkyl, heterocycloalkyl, aryl, heteroaryl, aralkyl, heteroaralkyl, alkoxy, and aryloxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, heterocycloalkyl, in which alkyl, alkenyl, alkynyl, alkyloxy, aryl, heteroaryl cycloalkyl, and heterocycloalkyl may further substituted.

The diamide compounds described above include their pharmaceutically acceptable salts and prodrugs, if applicable. Such a salt can be formed between a positively charged ionic group in an diamide compound (e.g., ammonium) and a negatively charged counterion (e.g., trifluoroacetate). Likewise, a negatively charged ionic group in a diamide compound (e.g., carboxylate) can also form a salt with a positively charged counterion (e.g., sodium, potassium, calcium, or magnesium). The diamide compounds may contain a non-aromatic double bond and one or more asymmetric centers. Thus, they can occur as racemic mixtures, single enantiomers, individual diastereomers, diastereomeric mixtures, and cis- or trans-isomeric forms. All such isomeric forms are contemplated.

Another aspect of this invention relates to a method of inhibiting DPP-IV by contacting the enzyme with one of the above-described compounds. Surprisingly, these diamide compounds preferentially inhibit the activity of DPP-IV over that of DPPII, DPP-VIII, or fibroblast activation protein. As inhibition of DPP-IV results in reduced blood glucose levels and enhanced insulin secretion, these compounds can be also used to treat Type II diabetes. Thus, this invention further covers a method of treating Type II diabetes by administering to a subject in need thereof an effective amount of one or more of the compounds.

Also within the scope of this invention is a pharmaceutical composition containing one or more of the above-described compounds and a pharmaceutically acceptable carrier, as well as use of the composition for the manufacture of a medicament for treating Type II diabetes.

The details of many embodiments of the invention are set forth in the description below. Other features, objects, and advantages of the invention will be apparent from the description and the claims.

DETAILED DESCRIPTION

The diamide compounds of this invention can be synthesized by synthetic methods well known in the art. Two exemplary synthetic routes are shown in Schemes 1 and 2 below.

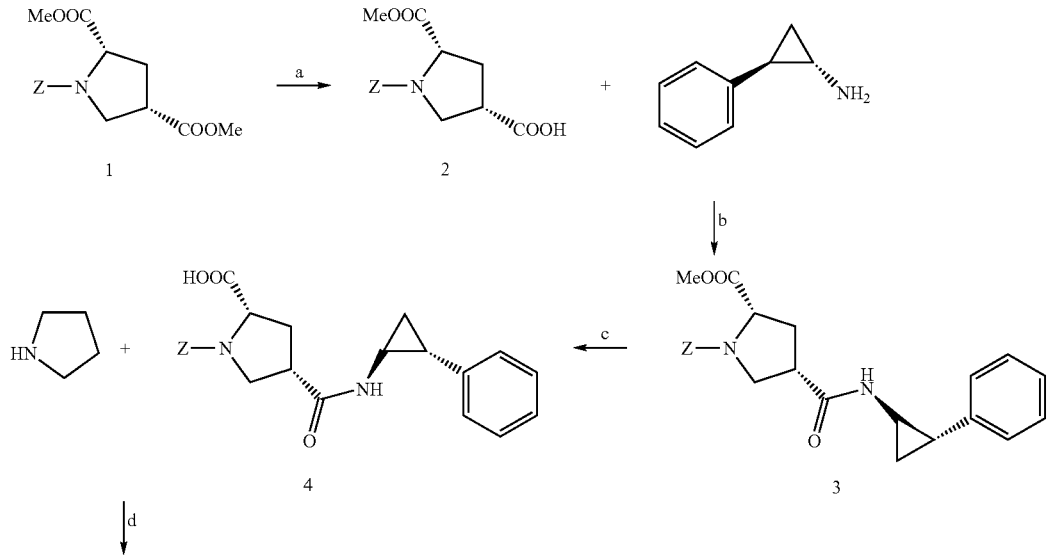

Scheme 1. (a) THF, NaOH 1N, 0.5 equiv, 30 min, 0° C. then 1 h, rt; (b) DCC, HOSu, CH₂Cl₂, 1,4-dioxane, 16 h, rt; (c) THF, NaOH 1N, 1.5 equiv, 30 min, 0° C. then 16 h, rt; (d) isobutyl chloroformate, 1-methylpiperidine, CH₂Cl₂, 30 min, -15° C. then 3 h, rt; (e) HBr/CH₃COOH, 15 min, rt.

In Scheme 1, the starting compound is a pyrrolidine diester (Compound 1) in which the amino group is protected. It can be made by the procedure described in *J. Med. Chem.* 1991, 34, 717. Partial hydrolysis of this compound produces a monoacid (Compound 2), which is reacted with isoindoline to give an amide intermediate (Compound 3). The intermediate contains an ester group. Hydrolysis of the ester group affords another monacid (Compound 4), which is subsequently coupled with a pyrrolidine compound to form a diamide (Compound 5). Removing the amino protecting group affords the desired diamide (Compound 6).

In Scheme 2, starting diester compound 7 can be made by the procedure described in *Tetrahedron* 1995, 51, 8545. Partial hydrolysis of this compound, followed by protecting the amino group, produces monoacid compound 8, which can be reacted with pyrrolidine-2-carboxylic acid amide to give an amide compound 9. Hydrolysis of the other ester group affords another monacid, which can be coupled with a 2-(3-trifluoromethyl-phenyl)-cyclopropylamine to form triamide compound 10. Dehydration converts a primary amide group to a cyano group. After the amino protecting group is removed, diamide compound 11 is formed.

The diamide compounds thus synthesized can be further purified by column chromatography, high performance liquid chromatography, or crystallization.

The above schemes demonstrate the syntheses of two specific diamide compounds of this invention. A skilled person in the art, in view of this example, would be able to modify the method to synthesize other diamide compounds of this invention. Alternatively, the skilled person can use other methods well known in the art to synthesize the diamide compounds of this invention.

Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic*

Synthesis, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The diamide compounds of this invention show effective inhibition against DPP-IV. Thus, this invention relates to a method of inhibiting DPP-IV by contacting the enzyme with an effective amount of one or more diamide compounds. Also included in this invention is a method of treating Type II diabetes by administering to a subject who needs the treatment an effective amount of one or more of the diamide compounds described above. The term "treating" refers to application or administration of the diamide compound to a subject, who has Type II diabetes, a symptom of Type II diabetes, or a predisposition toward Type II diabetes, with the purpose to cure, heal, alleviate, relieve, alter, remedy, ameliorate, improve, or affect the disease, the symptom, or the predisposition. "An effective amount" refers to the amount of the diamide compound which is required to confer the desired effect on the subject. Effective amounts vary, as recognized by those skilled in the art, depending on route of administration, excipient usage, and the possibility of co-usage with other therapeutic treatments such as use of other active agents.

To practice the treatment method of the present invention, a composition having one or more of the diamide compounds described above can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having an active diamide compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active diamide compound. Examples of other carriers include colloidal silicon oxide, magnesium stearate, cellulose, sodium lauryl sulfate, and D&C Yellow # 10.

The diamide compounds of this invention can be preliminarily screened by an in vitro assay for one or more of their desired activities, e.g., inhibiting DPP-IV. Compounds that demonstrate high activities in the preliminary screening can further be screened for their efficacy by in vivo assays. For example, a test compound can administered to an animal (e.g., a mouse model) having type II diabetes and its therapeutic effect is then accessed. Based on the results, an appropriate dosage range and administration route can also be determined.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All of the publications, including patents, cited herein are hereby incorporated by reference in their entirety.

EXAMPLE 1

Synthesis of 4-(2-phenyl-cyclopropylcarbamoyl)-2-(pyrrolidine-1-carbonyl-pyrrolidine hydrobromide (i) Preparation of cis-N-(benzyloxycarbonyl)-4-carboxy-proline methyl ester (compound 2)

A NaOH aqueous solution (1N, 10 mL) was added to a solution of N-(benzyloxycarbonyl)-4-carboxy-L-proline dimethyl ester (3.2 g, 10 mmol) in THF (20 mL) over a period of 60 min at 0° C. with stirring. After 30 min at 0° C. and 1 h at room temperature, the reaction mixture was concentrated and treated with EtOAc and 6 N HCl (5 mL). The organic layer was dried over $MgSO_4$ and concentrated. The residue was purified by a silica gel column using $CH_2Cl_2$/MeOH (95:5) as eluant to yield the desired compound as a colorless oil (2.1 g, 68%).

(ii) Preparation of 4-(2-phenyl-cyclopropylcarbamoyl)-pyrrolidine-1,2-dicarboxylic acid 1-benzyl ester 2-methyl ester (compound 3)

To a stirred solution of cis-N-(benzyloxycarbonyl)-4-carboxy-proline methyl ester (615 mg, 2 mmol) and HOSu (173 mg, 3 mmol) in 1,4-dioxane (2 mL) was added a solution of DCC (454 mg, 2.2 mmol) in $CH_2Cl_2$ (2 mL). After 10 min at room temperature, 2-phenylcyclopropylamine (266 mg, 2 mmol) in $CH_2Cl_2$ (1 mL) was added with stirring. After 16 h, the resulting N,N'-dicyclohexylurea was removed by filtration. The filtrate was washed with saturated aqueous $NaHCO_3$ (5 mL), 1 N aqueous citric acid (5 mL), water (5 mL), dried over $MgSO_4$ and concentrated. The residue was purified by a silica gel column using hexane/EtOAc (6:4) as eluant to yield the desired compound as a colorless oil (633 mg, 75%).

(iii) Preparation of 4-(2-phenyl-cyclopropylcarbamoyl)-pyrrolidine-1,2-dicarboxylic acid 1-benzyl ester (compound 4)

To a solution of 4-(2-Phenyl-cyclopropylcarbamoyl)-pyrrolidine-1,2-dicarboxylic acid 1-benzyl ester 2-methyl ester (422 mg, 1 mmol) in THF (2 mL) was added 1 N NaOH (1.5 mL) at 0° C. with stirring. After 30 min at 0° C. and 16 h at room temperature, the reaction mixture was concentrated and treated with EtOAc and 6 N HCl (5 mL). The organic layer was dried over $MgSO_4$ and concentrated. The residue was purified by a silica gel column using $CH_2Cl_2$/MeOH (95:5) as eluant to yield the desired compound as a colorless oil (343 mg, 84%).

(iv) Preparation of 4-(2-Phenyl-cyclopropylcarbamoyl)-2-(pyrrolidine-1-carbonyl-pyrrolidine-1-carboxylic acid benzyl ester (compound 5)

Isobutyl chloroformate (103 mg, 0.75 mmol) was added to a solution of 4-(2-Phenyl-cyclopropylcarbamoyl)-pyrrolidine-1,2-dicarboxylic acid 1-benzyl ester (306 mg, 0.75 mmol) and 1-methylpiperidine (75 mg, 0.75 mmol) in $CH_2Cl_2$ (15 mL) at −15° C. After 2 min at −15° C., pyrrolidine (57 mg, 0.8 mmol) in $CH_2Cl_2$ (1 mL) was added with stirring. After 30 min at −15° C. and 3 h at room temperature, the reaction mixture was washed with saturated aqueous $NaHCO_3$ (5 mL), 1 N aqueous citric acid (5 mL), water (5 mL), dried over $MgSO_4$ and concentrated. The residue was purified by a silica gel column using hexane/EtOAc (6:4) as eluant to yield the desired compound as a white solid (187 mg, 54%).

(v) Preparation of 4-(2-phenyl-cyclopropylcarbamoyl)-2-(pyrrolidine-1-carbonyl-pyrrolidine hydrobromide (compound 6)

4-(2-phenyl-cyclopropylcarbamoyl)-2-(pyrrolidine-1-carbonyl-pyrrolidine-1-carboxylic acid benzyl ester (115 mg, 0.25 mmol) was treated with 33% HBr in glacial AcOH (1 mL) at room temperature. After 15 min, the reaction solution was concentrated under the reduced pressure below 30° C. to give a brown crude product. The crude product was recrystallized from MeOH-Ether to afford a white solid (81 mg, 80%).

$^1$H NMR ($CDCl_3$, 300 MHz, δ): 7.70 (brs, NH), 7.26-7.21 (m, 2H), 7.17-7.11 (m, 3H), 3.93 (brs, 1H), 3.55-3.15 (m, 7H), 3.00-2.91 (m, 2H), 2.34 (dt, J=12.9, 8.4 Hz, 1H), 2.09-1.84 (m, 6H), 1.21-1.16 (m, 2H); MS ($ES^+$) m/z calcd. for $C_{19}H_{25}N_3O_2$: 327.42; found: 328.2 (M+H), 350.2 (M+Na).

EXAMPLE 2

Synthesis of (3S,5S)-5-(pyrrolidine-1-carbonyl)-N-((1S,2R)-2-(3-(trifluoromethyl)phenyl)cyclopropyl)pyrrolidine-3-carboxamide The desired compound was synthesized in the similar manner to compound 6.

$^1$H NMR ($CDCl_3$, 300 MHz, δ): 7.97 (brs, NH), 7.39-7.31 (m, 4H), 3.99 (t, J=7.5 Hz, 1H), 3.59-3.16 (m, 7H), 3.08-2.93 (m, 2H), 2.40 (dt, J=13.2, 9.0 Hz, 1H), 2.15-1.84 (m, 6H), 1.32-1.19 (m, 2H); MS ($ES^+$) m/z calcd. for $C_{20}H_{24}F_3N_3O_2$: 395.42; found: 396.1 (M+H), 418.1 (M+Na).

EXAMPLE 3

Synthesis of (3S,5S)-5-(pyrrolidine-1-carbonyl)-N-((1S,2R)-2-(4-(trifluoromethyl)phenyl)cyclopropyl)pyrrolidine-3-carboxamide The desired compound was synthesized in the similar manner to compound 6.

$^1$H NMR ($CDCl_3$, 300 MHz, δ): 7.89 (brs, NH), 7.48 (d, J=8.0 Hz, 2H), 7.22 (d, J=8.0 Hz, 2H), 4.02 (dd, J=7.2, 8.4 HZ, 1H), 3.61-3.18 (m, 7H), 3.09-2.91 (m, 2H), 2.38 (ddt, J=1.8, 13.2, 9.0 Hz, 1H), 2.15-1.85 (m, 6H), 1.35-1.18 (m, 2H); MS ($ES^+$) m/z calcd. for $C_{20}H_{24}F_3N_3O_2$: 395.42; found: 396.1 (M+H), 418.1 (M+Na).

EXAMPLE 4

Synthesis of (3S,5S)-N-((1S,2R)-2-(4-chlorophenyl)cyclopropyl)-5-(pyrrolidine-1-carbonyl)pyrrolidine-3-carboxamide The desired compound was synthesized in the similar manner to compound 6.

$^1$H NMR ($CDCl_3$, 300 MHz, δ,): 7.76 (brs, NH), 7.20 (d, J=8.4 Hz, 2H), 7.07 (d, J=8.4 Hz, 2H), 3.94 (dd, J=6.9, 8.1 Hz, 1H), 3.59-3.35 (m, 3H), 3.27-2.93 (m, 5H), 2.88-2.85 (m, 1H), 2.33 (ddt, J=1.5, 13.2, 9.0 Hz, 1H), 2.05-1.85 (m, 6H), 1.25-1.11 (m, 2H); MS ($ES^+$) m/z calcd. for $C_{19}H_{24}ClN_3O_2$: 361.87; found: 362.5 (M+H).

EXAMPLE 5

Synthesis of (3S,5S)-N-((1S,2R)-2-(3-fluorophenyl)cyclopropyl)-5-(pyrrolidine-1-carbonyl)pyrrolidine-3-carboxamide The desired compound was synthesized in the similar manner to compound 6.

$^1$H NMR ($CDCl_3$, 300 MHz, δ): 7.78 (brs, NH), 7.23-7.16 (m, 1H), 6.92-6.80 (m, 3H), 3.94 (dd, J=6.6, 8.4 Hz, 1H), 3.62-3.36 (m, 3H), 3.29-2.88 (m, 6H), 2.34 (dt, J=13.2, 9.0 Hz, 1H), 2.08-1.85 (m, 6H), 1.27-1.14 (m, 2H). MS ($ES^+$) m/z calcd. for $C_{19}H_{24}FN_3O_2$: 345.41; found: 346.5 (M+H), 368.5 (M+Na).

EXAMPLE 6

Synthesis of (2S,4S,5S)-1-{5-methyl-4-[2-(3-trifluoromethyl-phenyl)-cyclopropanecarbonyl]-pyrrolidine-2-carbonyl}-pyrrolidine-2-carbonitrile (compound 11)

(i) Preparation of (2S,4S,5S)-5-methyl-pyrrolidine-1,2,4-tricarboxylic acid 1-tert-butyl ester 4-methyl ester (compound 8)

A solution of (2S,4S,5S)-5-methylpyrrolidine-2,4-dicarboxylic acid 2-tert-butyl ester 4-methyl ester (730 mg, 3 mmol) in TFA (5 mL) was stirred at room temperature for 30 min. The reaction mixture was concentrated in vacuo. The resultant residue was dissolved in $CH_2Cl_2$ (8 mL). Triethylamine (607 mg, 6 mmol) was then added, followed by di-tert-butyldicarbonate (980 mg, 4.5 mmol) in $CH_2Cl_2$ (3 mL). After stirred at 0° C. for 30 min and at room temperature for 8 h, the reaction mixture was concentrated in vacuo, dissolved in $CH_2Cl_2$ (50 mL), and extracted with 1 N aqueous citric acid (10 mL). The organic layer was dried over $MgSO_4$ and concentrated. The residue was purified by a silica gel column using $CH_2Cl_2$/MeOH (95:5) as eluent to yield compound 8 (517 mg, 1.8 mmol, 60%).

(ii) Preparation of (2S,4S,5S)-5-(2-carbamoyl-pyrrolidine-1-carbonyl)-2-methyl-pyrrolidine-1,3-dicarboxylic acid 1-tert-butyl ester 3-methyl ester (9)

A solution of DCC (454 mg, 2.2 mmol) in $CH_2Cl_2$ (3 mL) was added to a stirred solution of compound 8 (517 mg, 1.8 mmol), 4-DMAP (439 mg, 3.6 mmol) and HOBt (316 mg, 2.3 mmol) in 1,4-dioxane (3 mL). After 10 min at room temperature, (S)-pyrrolidine-2-carboxamide (251 mg, 2.2 mmol) in $CH_2Cl_2$ (2 mL) was added with stirring. The reaction mixture was stirred for 16 h and was then filtered. The filtrate was washed with saturated aqueous $NaHCO_3$ (5 mL), 1 N aqueous citric acid (5 mL), water (5 mL), dried over $MgSO_4$, and concentrated. The residue was purified by a silica gel column using $CH_2Cl_2$/MeOH (95:5) as eluent to yield compound 9 (586 mg, 1.5 mmol, 85%).

(iii) Preparation of (2S,4S,5S)-5-(2-Carbamoyl-pyrrolidine-1-carbonyl)-2-methyl-3-[2-(3-trifluoromethyl-phenyl)-cyclopropanecarbonyl]-pyrrolidine-1-carboxylic acid tert-butyl ester (compound 10)

To a solution of compound 9 (586 mg, 1.5 mmol) in THF (3 mL) was added 1 N NaOH (2.5 mL) at 0° C. with stirring. After 30 min at 0° C. and 3 h at room temperature, the reaction mixture was concentrated and then treated with EtOAc and 6 N HCl (6 mL). The organic layer was dried over $MgSO_4$ and concentrated. The residue was purified by a silica gel column using $CH_2Cl_2$/MeOH (95:5) as eluent to yield an acid compound (553 mg, 1.5 mmol, 99%).

To a stirred solution of the acid compound (553 mg, 1.5 mmol), 4-DMAP (366 mg, 3.0 mmol) and HOBt (275 mg, 2.0 mmol) in 1,4-dioxane (2 mL) was added a solution of DCC (454 mg, 2.2 mmol) in $CH_2Cl_2$ (2 mL). After 10 min at room temperature, 2-(3-(trifluoromethyl)phenyl)cyclopropanamine hydrochloride (380 mg, 1.6 mmol) and triethylamine (162 mg, 1.6 mmol) in $CH_2Cl_2$ (2 mL) were added. The reaction mixture was stirred for 16 h and filtered. The filtrate was washed with saturated aqueous $NaHCO_3$ (5 mL), 1 N aqueous citric acid (5 mL), water (5 mL), dried over $MgSO_4$, and concentrated. The residue was purified by a silica gel column using $CH_2Cl_2$/MeOH (95:5) as eluent to yield compound 10 (607 mg, 1.1 mmol, 73%).

(iv) Preparation of (2S,4S,5S)-1-{5-Methyl-4-[2-(3-trifluoromethyl-phenyl)-cyclopropanecarbonyl]-pyrrolidine-2-carbonyl}-pyrrolidine-2-carbonitrile (compound 11)

Phosphoryl chloride (674 mg, 4.4 mmol) was slowly added to a mixture of compound 10 (607 mg, 1.1 mmol), imidazole (112 mg, 1.6 mmol), and pyridine (5 mL) at −30° C. over a period of 5 min. The resultant cloudy white reaction mixture was stirred at −30° C. for 1 h. The resultant light yellow opaque mixture was concentrated in vacuo and treated with $CH_2Cl_2$ and 1 N aqueous citric acid (5 mL). The organic layer was dried over $MgSO_4$ and concentrated. The residue was purified by a silica gel column using $CH_2Cl_2$/EtOAc (1:1) as eluant to yield a crude product (506 mg, 0.9 mmol, 82%), which was stirred in TFA (5 mL) at room temperature for 30 min. The reaction mixture was concentrated in vacuo to yield the desire TFA salt compound 11 without further purification.

$^1$H NMR ($CD_3OD$, 300 MHz, δ): 7.47-7.39 (m, 4H), 4.87-4.80 (m, 1H), 4.62 (dd, J=9.0, 9.3 Hz, 1H), 3.99-3.90 (m, 1H), 3.61 (t, J=6.6 Hz, 2H), 3.20-3.13 (m, 1H), 2.97-2.79 (m, 2H), 2.36-2.08 (m, 6H), 1.44 (d, J=1.5, 6.9 Hz, 3H), 1.34-1.26 (m, 2H); MS ($ES^+$) m/z calcd. for $C_{22}H_{25}F_3N_4O_2$: 434.45; found: 435.3 (M+H).

EXAMPLE 7

Inhibition of DPP-IV and DPP-VIII Activity

DPP-IV was purified from human semen according to the method described in de Meester et al. (de Meester et al. (1996) J. Immun. Method 189: 99-105) with minor modifications. Briefly, the semen was diluted with 50 mL of phosphate buffered saline (PBS) and centrifuged at 900×g for 10 minutes. The supernatant was centrifuged again at 105,000×g for 120 minutes to separate prostasomes and seminal plasma. The prostasomes, i.e., pellets, and the seminal plasma, i.e., supernatant, were both used for further purification of DPP-IV. The pellets were washed twice with 20 mM Tris-HCl (pH 7.4), and then incubated in 20 mM Tris-HCl (pH 7.4), 1% Triton X-100 for 1 hour at 4° C. The resulting solution was centrifugated at 40,000×g for 10 minutes to remove prostasomes debris before dialyzed against 20 mM Tris-HCl (pH 7.4), 70 mM NaCl, and 0.1% Triton X-100. The solution was then passed through a DEAE-Sepharose fast flow column (2.6×10 cM) equilibrated with 20 mM Tris-HCl (pH 7.4), 70 mM NaCl and 0.1% Triton X-100 at a flow rate of 2 mL/min. The column was subsequently eluted with 300 mL NaCl (70 to 350 mM) with a linear gradient at a flow rate of 3 mL/min. Positive fractions were pooled and adjusted to pH 8.0 by 0.5 M Tris-HCl (pH 8.0) before applied to an adenosine deaminase-Sepharose columns. The column was prepared as described in de Meester et al. After the column was washed with 10 column volumes of equilibration buffer and then with an equal amount of 50 mM Tris-HCl (pH 7.4) containing 0.5 M NaCl and 0.1% Triton X-100, DPP-IV was eluted with 2 mM Tris-HCl (pH 8.0) containing 0.1% Triton X-100. The supernatant was denatured in 20 mM Tris-HCl (pH 7.4), 1% Tris X-100 for 1 hour at 4° C. The resulting solution was handled as described above to obtain purified DPP-IV.

DPP-VIII was also expressed and purified. Briefly, full length Human DPP-VIII cDNA was amplified by RT-PCR from a human liver cDNA library with the primers 5'-AAGCTTCCATGGCAGCAGCAATGGAAACA-3' (SEQ ID NO:1) and 5'-GCGGCCGCTTATATCACTTTTAGAGCAGCAATA-3' (SEQ ID NO:2). The resulting fragments were cloned into pCR®-Blunt II-Topo vector (Invitrogen). The full length DPP-VIII cDNA fragment was released by digestion with HindIII (blunt) and Not I, and then ligated into the baculovirus expression vector pBac-PAC-His2 (Clontech). The plasmid was transfected into Sf9 cells to obtain recombinant virus. Further amplifications of the virus were conducted. Briefly, virus titers were determined by end-point dilution assays. Baculovirus infections were carried out as follows: the Sf9 cells were cultured in 6-well plates to reach a concentration of $10^6$ cells per well. The culture media were removed and replaced by virus inoculum at a multiplicity of infection (M.O.I.) of 0.1 $TCID_{50}$/cell ($TCID_{50}$ is 50% tissue-culture infectious dose). After removing media containing the unbound virus, fresh media were added and the cells were incubated at 27° C. for 72 to 96 hours. The Sf9 cells were infected at an M.O.I. of 0.5 $TCID_{50}$/cell and were harvested at 72 hours post-transfection for subsequent protein purification. The purification of DPP-VIII was done by a Ni-NTA column. The Sf9 cells expressing DPP-VIII were pelleted and resuspended in binding buffer containing 50 mM sodium phosphate buffer (pH 7.6) and 300 mM NaCl. The cells were sonicated and the cleared lysates were passed through a Ni-affinity column. The column was washed by three to five bed volume of a binding buffer containing 10 mM imidazole, a binding buffer containing 30 mM imidazole, and a binding buffer containing 120 mM imidazole. Note that expression of DPP-VIII was tracked by fluorescent eGFP expression or protein activity assays.

The purity of DPP-IV and DPP-VIII was checked by SDS-PAGE, followed by commassie blue stain or silver stain. Concentrations of DPP-IV and DPP-VIII were measured by the method of Bradford using BSA as the standard (Bradford, M. M. (1976) *Anal. Biochem.* 72, 248-254.)

The biological activities of DPP-IV and DPP-VIII were confirmed by measuring enzymatic kinetic constants. As an example, the kinetic constant of DPP-IV was measured as follows:

All reactions were carried out in PBS using

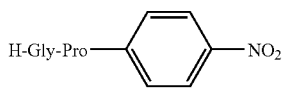

as a substrate in the presence of 10 nM DPP-IV. The reactions were monitored and measured at OD 405 nm. The initial rate was measured when less than 10% substrate was depleted. The steady state parameters, $k_{cat}(=V_{max}/[E])$ and $K_m$, were determined from initial velocity measurements at 0.5-5 $K_m$ of the substrate concentrations for the first 300 seconds. Lineweaver-Burk plots were obtained using non-linear regression of the classic Michaelis-Menten equation (equation 1) to obtain $K_m$ values. The $k_{cat}$ was calculated from $V_{max}/[E]$ with the molecular weight of DPP-IV taken as 85,000.

$$V_0 = V_{max}[S]/(K_m+[S]) \quad \text{(equation 1)}$$

where $V_0$ is the initial velocity, [S] is the substrate concentration, $V_{max}$ is the maximum velocity and $K_m$ is the Michaelis constant. Correlation coefficients better than 0.990 were obtained throughout.

A number of compounds of this invention were tested for their inhibitory effects against DPP-IV and DPP-VIII. For each compound, eight to twelve serial dilutions were used to generate data points, from which the $IC_{50}$ value was calculated based on the Sigma plot. All tested compounds exerted inhibitory activities against DPP-IV with low $IC_{50}$ values, e.g., 2 nM-1 µM. Surprisingly, all tested compounds preferentially inhibited DPP-IV over DPP-VIII.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the diamide compounds of this invention also can be made, screened for their inhibitory activities against DPP-IV and treating Type II diabetes and used to practice this invention. Thus, other embodiments are also within the claims.

What is claimed is:

1. A compound of the following formula:

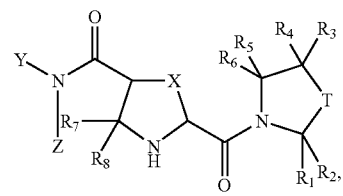

wherein

T is $C(R_9R_{10})$, NH, O, or S;

X is $(CR_{11}R_{12})_n$, n being 1 or 2;

Y is cycloalkyl, and Z is H, alkyl, optionally substituted cycloalkyl, heterocycloalkyl, aryl, heteroaryl, arylalkyl, carbonyl;

each of $R_1$, $R_2$, $R_5$, $R_6$, $R_7$, and $R_8$, independently, is H, alkyl, cyano, nitro, cycloalkyl, heterocycloalkyl, aryl or heteroaryl; each of $R_3$, $R_4$, $R_9$, $R_{10}$, $R_{11}$, and $R_{12}$, independently, is H, alkyl, halo, cyano, nitro, alkoxyl, hydroxyl, cycloalkyl, heterocycloalkyl, aryl, or heteroaryl.

2. The compound of claim 1, wherein X is $CH_2$.

3. The compound of claim 2, wherein T is O, S, or $CH_2$.

4. The compound of claim 3, wherein $R_1$ is cyano, and each of $R_2$, $R_3$, $R_4$, $R_5$, $R_6$, $R_7$, $R_8$, $R_9$, $R_{10}$, $R_{11}$, and $R_{12}$, is H.

5. The compound of claim 3, wherein $R_3$ is F, $R_4$ is H or F, and each of $R_1$, $R_2$, $R_5$, $R_6$, $R_7$, $R_8$, $R_9$, $R_{10}$, $R_{11}$, and $R_{12}$, is H.

6. The compound of claim 3, wherein $R_7$ is $CH_3$, and $R_8$ is H or $CH_3$.

7. The compound of claim 1, wherein T is O, S, $CH_2$.

8. The compound of claim 1, wherein T is $CH_2$.

9. The compound of claim 1, wherein Y is cycloalkyl, and Z is H, alkyl, cycloalkyl, heterocycloalkyl, aryl, heteroaryl, arylalkyl, carbonyl, or hydroxyl.

10. The compound of claim 1, wherein X is $C(CH_3)_2$.

11. The compound of claim 10, wherein Y is cycloalkyl, and Z is H, alkyl, cycloalkyl, heterocycloalkyl, aryl, heteroaryl, arylalkyl, carbonyl, or hydroxyl.

12. The compound of claim 11, wherein T is O, S, or $CH_2$.

13. The compound of claim 1, wherein the compound is

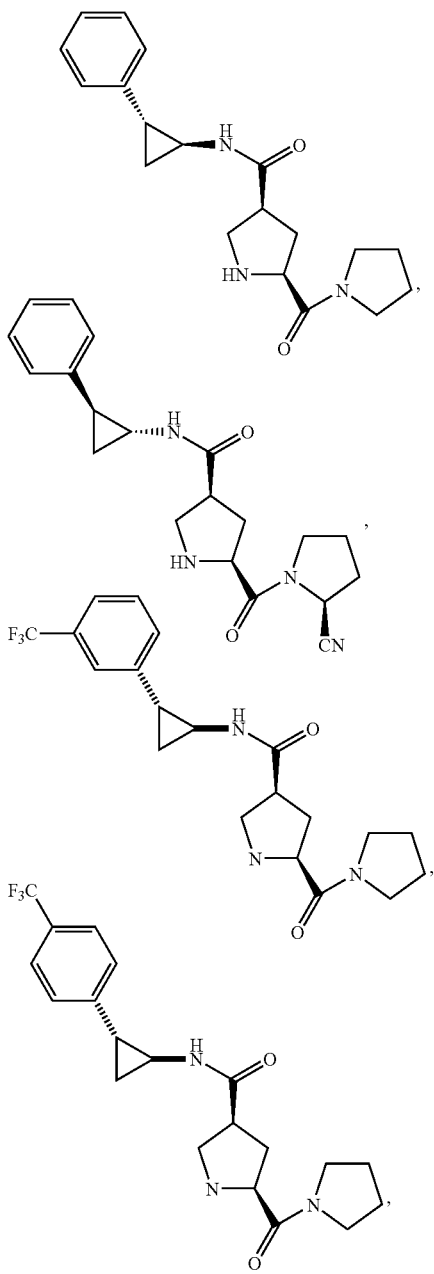

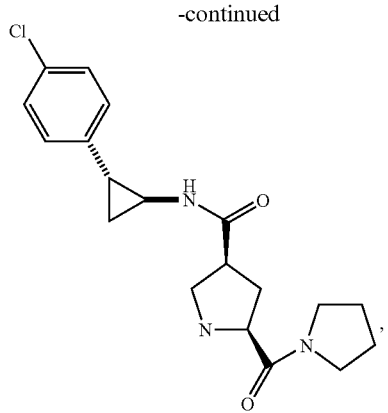

-continued

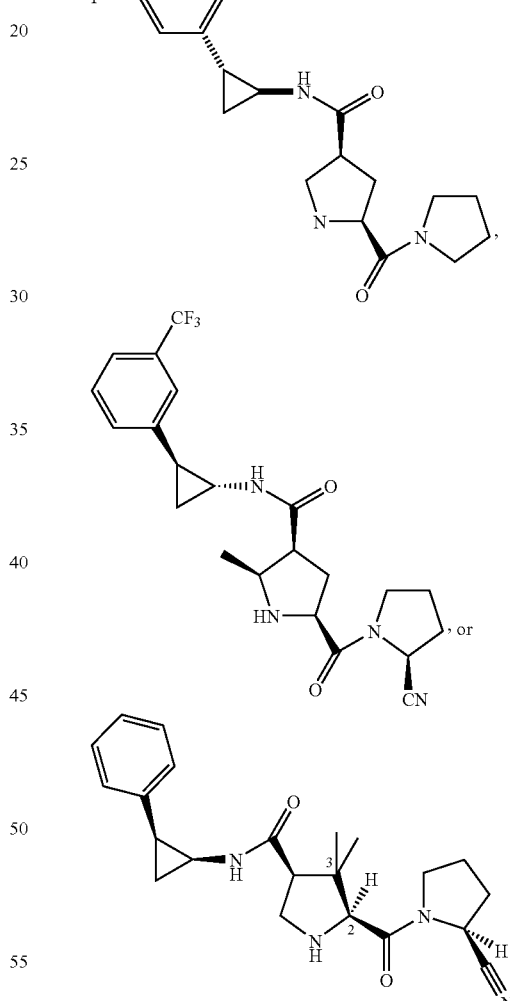

14. A method of inhibiting dipeptidyl peptidase IV, comprising contacting dipeptidyl peptidase IV with an effective amount of a compound of claim 1.

15. The method of claim 14, wherein Y is cycloalkyl, and Z is H alkyl, cycloalkyl, heterocycloalkyl, aryl, heteroaryl, arylalkyl, carbonyl or hydroxyl.

16. The method of claim 14, wherein Y is cyclopropyl.

17. The method of claim 14, wherein the compound is

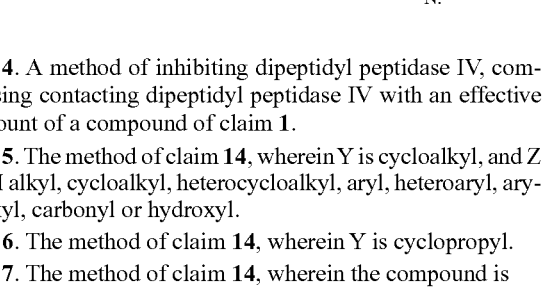

-continued
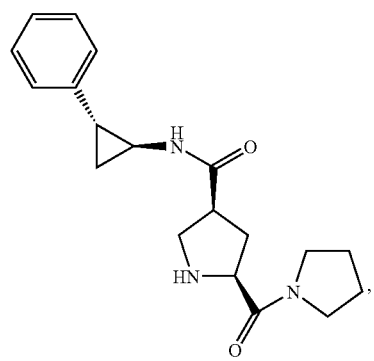
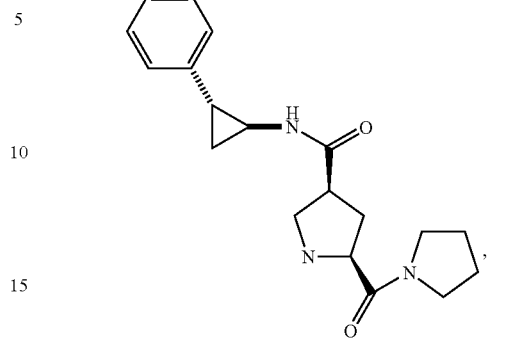
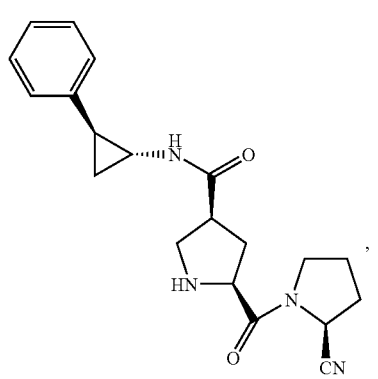
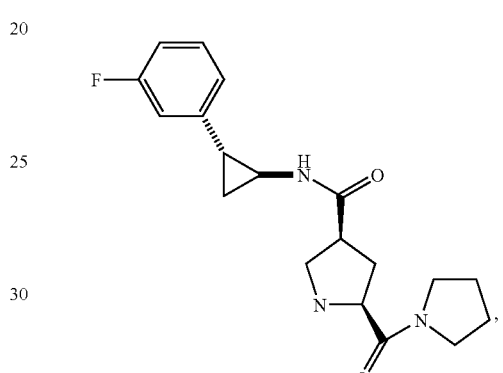
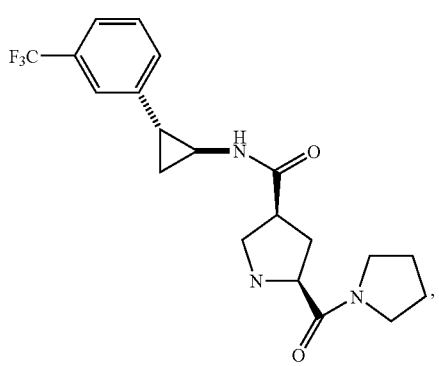
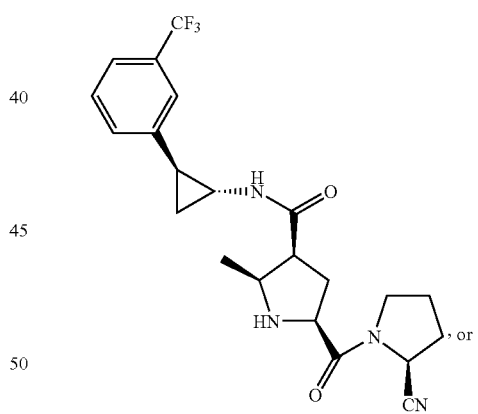
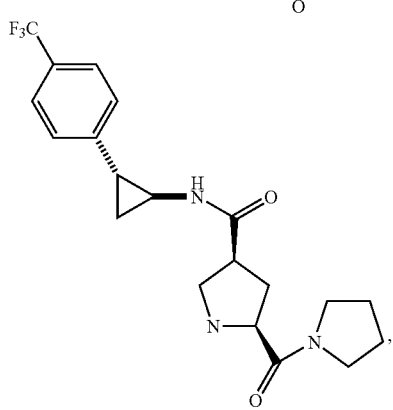
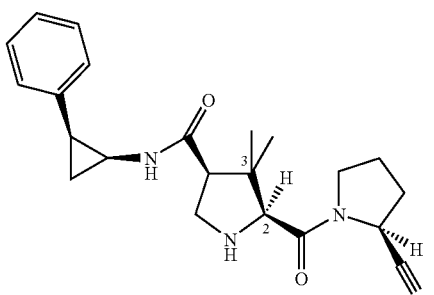

18. The compound of claim 9, wherein Y is cyclopropyl.
19. The compound of claim 18, wherein T is O, S, or $CH_2$.
20. The compound of claim 19, wherein $R_1$ is cyano, and each of $R_2$, $R_3$, $R_4$, $R_5$, $R_6$, $R_7$, $R_8$, $R_9$, $R_{10}$, $R_{11}$, and $R_{12}$, is H.
21. The compound of claim 19, wherein $R_3$ is F, $R_4$ is H or F, and each of $R_1$, $R_2$, $R_5$, $R_6$, $R_7$, $R_8$, $R_9$, $R_{10}$, $R_{11}$, and $R_{12}$, is H.
22. The compound of claim 19, wherein $R_7$ is $CH_3$, and $R_8$ is H or $CH_3$.
23. The compound of claim 18, wherein X is $CH_2$.
24. The compound of claim 22, wherein T is $CH_2$.
25. The compound of claim 13, wherein the compound is

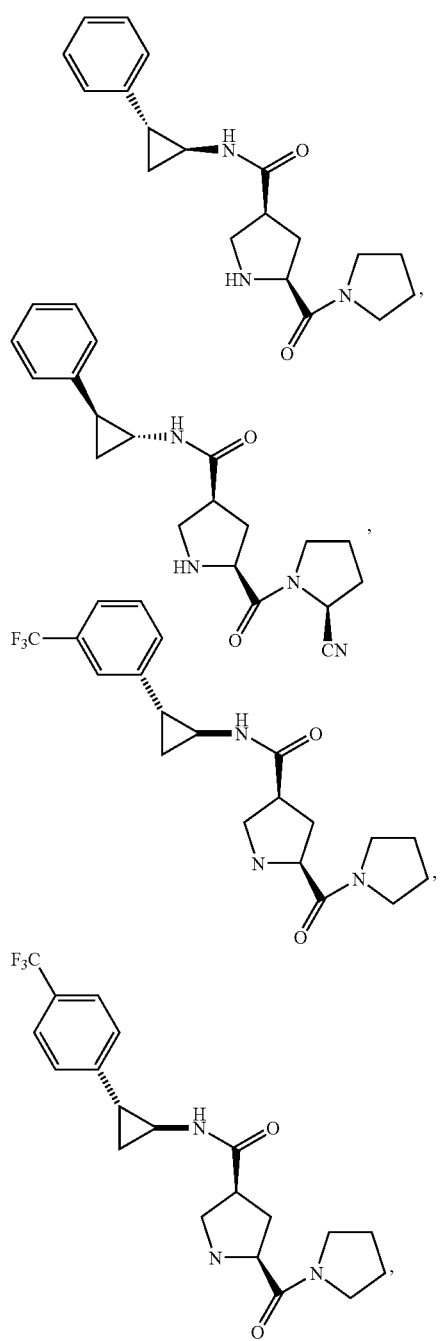

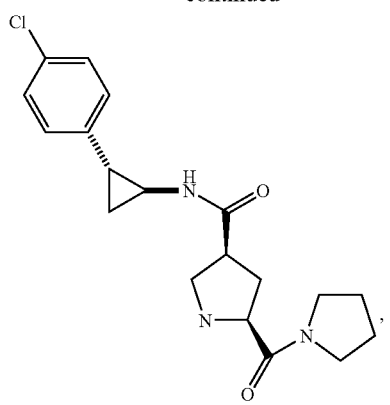

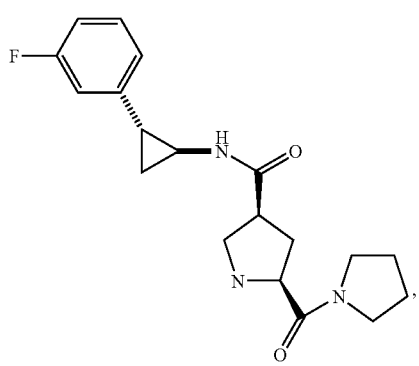

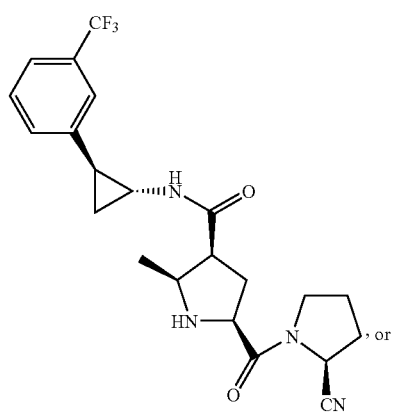

, or

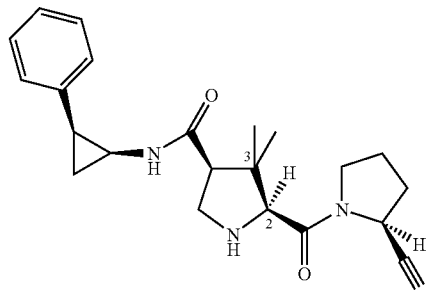

.

* * * * *